US006021343A

United States Patent [19]
Foley et al.

[11] Patent Number: 6,021,343
[45] Date of Patent: Feb. 1, 2000

[54] IMAGE GUIDED AWL/TAP/SCREWDRIVER

[75] Inventors: Kevin T. Foley, Memphis, Tenn.;
Anthony J. Melkent, Lafayette, Colo.;
Catalina J. Carroll, Memphis, Tenn.

[73] Assignee: Surgical Navigation Technologies,
Broomfield, Colo.

[21] Appl. No.: 08/971,126

[22] Filed: Nov. 20, 1997

[51] Int. Cl.$^7$ .................................................. A61B 5/00
[52] U.S. Cl. ......................... 600/429; 606/130; 600/417
[58] Field of Search .................................. 600/407, 429,
600/473, 476, 417; 606/130, 79, 80, 96,
60–62, 104

[56] References Cited

U.S. PATENT DOCUMENTS

| D. 387,427 | 12/1997 | Bucholz et al. ........................ D24/140 |
| 3,963,028 | 6/1976 | Cooley et al. ............................ 128/276 |
| 4,672,306 | 6/1987 | Thong ..................................... 324/72.5 |
| 4,673,352 | 6/1987 | Hansen ..................................... 433/69 |
| 4,722,056 | 1/1988 | Roberts et al. ........................ 364/413 |
| 4,836,778 | 6/1989 | Baumrind et al. ........................ 433/69 |
| 5,050,608 | 9/1991 | Watanabe et al. ....................... 128/653 |
| 5,078,140 | 1/1992 | Kwoh .................................... 128/653.1 |
| 5,186,174 | 2/1993 | Schlöndorff et al. .................... 128/653 |
| 5,198,877 | 3/1993 | Schulz ..................................... 356/375 |
| 5,207,681 | 5/1993 | Ghadjar et al. ............................ 606/96 |
| 5,230,623 | 7/1993 | Guthrie et al. ............................. 433/72 |
| 5,251,127 | 10/1993 | Raab ..................................... 364/413 |
| 5,295,483 | 3/1994 | Nowacki et al. ................... 128/660.03 |
| 5,299,288 | 3/1994 | Glassman et al. ........................ 395/80 |
| 5,305,203 | 4/1994 | Raab ..................................... 364/413 |
| 5,383,454 | 1/1995 | Bucholz .................................. 128/653.1 |
| 5,389,101 | 2/1995 | Heilbrun et al. ........................ 606/130 |
| 5,437,212 | 8/1995 | Thompson et al. ....................... 81/63.1 |
| 5,447,154 | 9/1995 | Cinquin et al. ....................... 128/653.1 |
| 5,474,558 | 12/1995 | Neubardt . |
| 5,517,990 | 5/1996 | Kalfas et al. ........................... 128/653 |
| 5,564,437 | 10/1996 | Bainville et al. . |
| 5,575,192 | 11/1996 | Eggert ..................................... 81/63.1 |
| 5,591,207 | 1/1997 | Coleman . |
| 5,617,857 | 4/1997 | Chader et al. ........................ 128/653.1 |
| 5,622,170 | 4/1997 | Schulz ..................................... 128/653 |
| 5,645,545 | 7/1997 | Bryant . |
| 5,662,111 | 9/1997 | Cosman .............................. 128/653.1 |
| 5,676,673 | 10/1997 | Ferre et al. ............................. 606/130 |
| 5,682,890 | 11/1997 | Kormos et al. . |
| 5,732,703 | 3/1998 | Kalfas et al. . |
| 5,772,594 | 6/1998 | Barrick . |
| 5,810,828 | 9/1998 | Lightman et al. . |
| B1 5,383,454 | 12/1996 | Bucholz .............................. 128/653.1 |

FOREIGN PATENT DOCUMENTS

| 1336451 | 1/1988 | Canada . |
| 0 326 768 | 12/1988 | European Pat. Off. . |
| 0 501 993 B1 | 11/1990 | European Pat. Off. . |
| 0 469 966 A1 | 7/1991 | European Pat. Off. . |

(List continued on next page.)

OTHER PUBLICATIONS

C. Hunter Shelden, M.D, et al., "Development of a computerized microstereotaxic method for localization and removal of minute CNS lesions under direct 3–D vision," J. Neurosurg 52: 21–27, 1980.

(List continued on next page.)

*Primary Examiner*—William E. Kamm
*Assistant Examiner*—Shawna J Shaw
*Attorney, Agent, or Firm*—Finnegan, Henderson, Farabow, Garrett & Dunner, L.L.P.

[57] ABSTRACT

A trackable medical instrument for use in a computer assisted image guided medical and surgical navigation systems that generate images during medical and surgical procedures, includes a guide member having an emitter array for being tracked by the system and a drive shaft contained within the guide member having a proximal and a distal end, the drive shaft being rotatable within the guide member while being fixable axially inside the guide member, the proximal end of the drive shaft having a first connector for interchangeably receiving at least one drive source, and the distal end having a second connector for interchangeably receiving at least one instrument tip.

50 Claims, 5 Drawing Sheets

FOREIGN PATENT DOCUMENTS

| | | |
|---|---|---|
| WO 90/05494 | 5/1990 | WIPO . |
| WO 91/04711 | 4/1991 | WIPO . |
| WO 91/07726 | 5/1991 | WIPO . |
| WO 92/06645 | 4/1992 | WIPO . |
| WO 94/23647 | 10/1994 | WIPO . |
| WO 94/24933 | 11/1994 | WIPO . |
| WO 96/11624 | 4/1996 | WIPO . |
| WO96/11624 | 4/1996 | WIPO . |
| WO97/15234 | 5/1997 | WIPO . |

OTHER PUBLICATIONS

M. Peter Heilbrun, M.D., "Computer Tomography–Guided Stereotactic Systems," Computed Tomographic Stereotaxy, Ch.31 pp. 564–581, 1983.

Richard D. Bucholz, M.D. and K. Charles Cheung, M.D., "Halo vest versus spinal fusion for cervical injury: evidence from an outcome study," J. Neurosurg 70:884–892, Jun. 1989.

W. Krybus, et al., "Navigation Support for Surgery by Means of Optical Position Detection," p. 362–366, 1990.

Kurt R. Smith and Richard D. Bucholz, "Computer Methods for Improved Diagnostic Image Display Applied to Stereotactic Neurosurgery," Stereotactic Neurosurgery Display, vol. 14, pp. 371–382, 1992.

L. Adams, et al., "Aide Au Reperage Tridimensionnel Pour La Chirurgie de la Base du Crane," Innov. Tech. Biol. Med., vol. 13, No. 4, pp. 409–424, 1992.

Hans F. Reinharts, M.D., et al., "Sonic Stereometry in Microsurgical Procedures for Deep–Seated Brain Tumors and Vascular Malformations," Neurosurgery, vol. 32, No. 1, Jan. 1993 pp. 51–57.

Skip Jacques, et al., "A Computerized Microstereotactic Method to Approach, 3–Dimensionally Reconstruct, Remove and Adjuvantly Treat Small CNS Lesions," Meeting of the Amer. Soc. Stereotactic & Functional Neurosurgery, Houston 1980, Appl. Neurophysiol. 43: 176–182 (1980).

Richard D. Bucholz, M.D., and Kurt R. Smith, "A Comparison of Sonic Digitizers Versus Light Emitting Diode–Based Localization," Interactive Image–Guided Neurosurgery, pp. 179–200, 1993.

Richard D. Bucholz, et al., "Clinical Applications of Modern Imaging Technology," SPIE vol. 1894 pp. 312–322, Jan. 19, 1993.

Richard D. Bucholz, et al., "Intraoperative localization using a three dimensional optical digitizer," Proceedings of Clinical Applications of Modern Imaging Technology, vol. 1894, pp. 312–322, 1993.

Kevin T. Foley, et al., "Image–guided Intraoperative Spinal Localization," Intraoperative Neuroprotection: Monitoring, Ch. 19, pp. 325–340, 1996.

Kurt R. Smith, et al., "The Neurostation™ —A Highly Accurate, Minimally Invasive Solution To Frameless Stereotactic Neurosurgery," Computerized Medical Imaging and Graphics, Jul.–Aug. 1994, vol. 18, No. 4, pp. 247–256.

Isabelle M. Germano, "The NeuroStation System for Image–Guided, Frameless Stereotaxy," Neurosurgery, vol. 37, No. 2, Aug. 1995, pp. 348–350.

Offset Probe for SAC GP8–3d Digitizer, 2 pages, not dated.

"Alignment Procedure for the PixSys Two–Emitter Offset Probe for the SAC GP–8–3d Sonic Digitizer," PixSys, Jul. 2, 1992, 4 pages.

"3–D Digitizing Accessories," PixSys, Jul. 2, 1992, 6 pages.

Richard D. Bucholz, M.D., et al., "Poster #1120, Use of an Intraoperative Optical Digitizer in a System for Free–Hand Stereotactic Surgery," Scientific Program, Am. Assoc. of Neurological Surgeons 1992 Annual Meeting, pp. 284–285, Apr. 16, 1992.

IMAGE GUIDED AWL/TAP/SCREWDRIVER

BACKGROUND OF THE INVENTION

1. Field of the Invention

The present invention relates generally to computer assisted image guided medical and surgical navigation systems that generate images during medical and surgical procedures indicating the relative position of various body parts, surgical implants, and instruments. In particular, the present invention relates to an instrument for use in an image guided surgery navigation system that enables the system to track both the depth and the trajectory of the instrument during surgery.

2. Background of Related Art

Computer assisted image guided medical and surgical navigation systems are known and used to generate images in order to guide a doctor during a surgical procedure. Such systems are disclosed, for example, in U.S. Pat. No. 5,383,454 to Bucholz; PCT application Ser. No. PCT/US94/04530 (Publication No. WO 94/24933) to Bucholz; and PCT application Ser. No. PCT/US95/12984 (Publication No. WO 96/11624) to Bucholz et al., incorporated herein by reference.

In general, these image guided systems use images of a body part, such as CT scans, taken before surgery to generate images on a display, such as a CRT monitor screen, during surgery for representing the position of a surgical instrument with respect to the body part. The systems typically include tracking devices such as, for example, an LED array mounted on a surgical instrument as well as a body part, a digitizer to track in real time the position of the body part and the instrument used during surgery, and a monitor screen to display images representing the body and the position of the instrument relative to the body part as the surgical procedure is performed.

There is a need in the art for a surgically navigable tool for use with these image guided systems that is simple to use and manipulate, that enables the computer tracking system to track both the trajectory of the instrument and the depth that the instrument is inserted into the body, and that is easily interchangeable with alternative drive sources such as a ratcheting handle or other instruments such as awls, taps, and screwdrivers.

SUMMARY OF THE INVENTION

It is therefore an object of the invention to provide an image guided medical instrument whose tip and trajectory can be simultaneously tracked.

It is a further object of the invention to provide an image guided medical instrument capable of generating a signal representing the trajectory and the depth of the tip of the instrument.

It is a still further object of the invention to provide an image guided medical instrument that may easily be used with any number of different tips and handles.

It is another object of the invention to provide an image guided medical instrument that is of relatively simple construction and relatively easy to use.

Additional objects and advantages of the invention will be set forth in the description which follows and, in part, will be obvious from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a trackable medical instrument for use in a computer assisted image guided surgery system having a digitizer for tracking the position of the instrument in three dimensional space and a display providing an indication of the position of the instrument with respect to images of a body part taken preoperatively. The instrument includes a guide member having an emitter array mounted thereon for being tracked by the digitizer, and a drive shaft contained within the guide member, the drive shaft having a proximal and a distal end, the drive shaft being rotatable within the guide member while being fixable axially within the guide member, the proximal end of the drive shaft having a first connector for interchangeably receiving at least one drive source, and the distal end having a second connector for interchangeably receiving at least one instrument tip. The instrument may further include at least one instrument tip for connection to the distal end of the drive shaft and a drive handle for connection to the proximal end of the drive shaft for transmitting torque to the instrument tip to cause rotation of the instrument tip.

In another aspect of this invention, the instrument may further include a sensor which senses the removal and the connection of an instrument tip to the instrument. The sensor may be an electromechanical switch on the guide member.

It is to be understood that both the foregoing general description and the following detailed description are exemplary and explanatory and are not restrictive of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
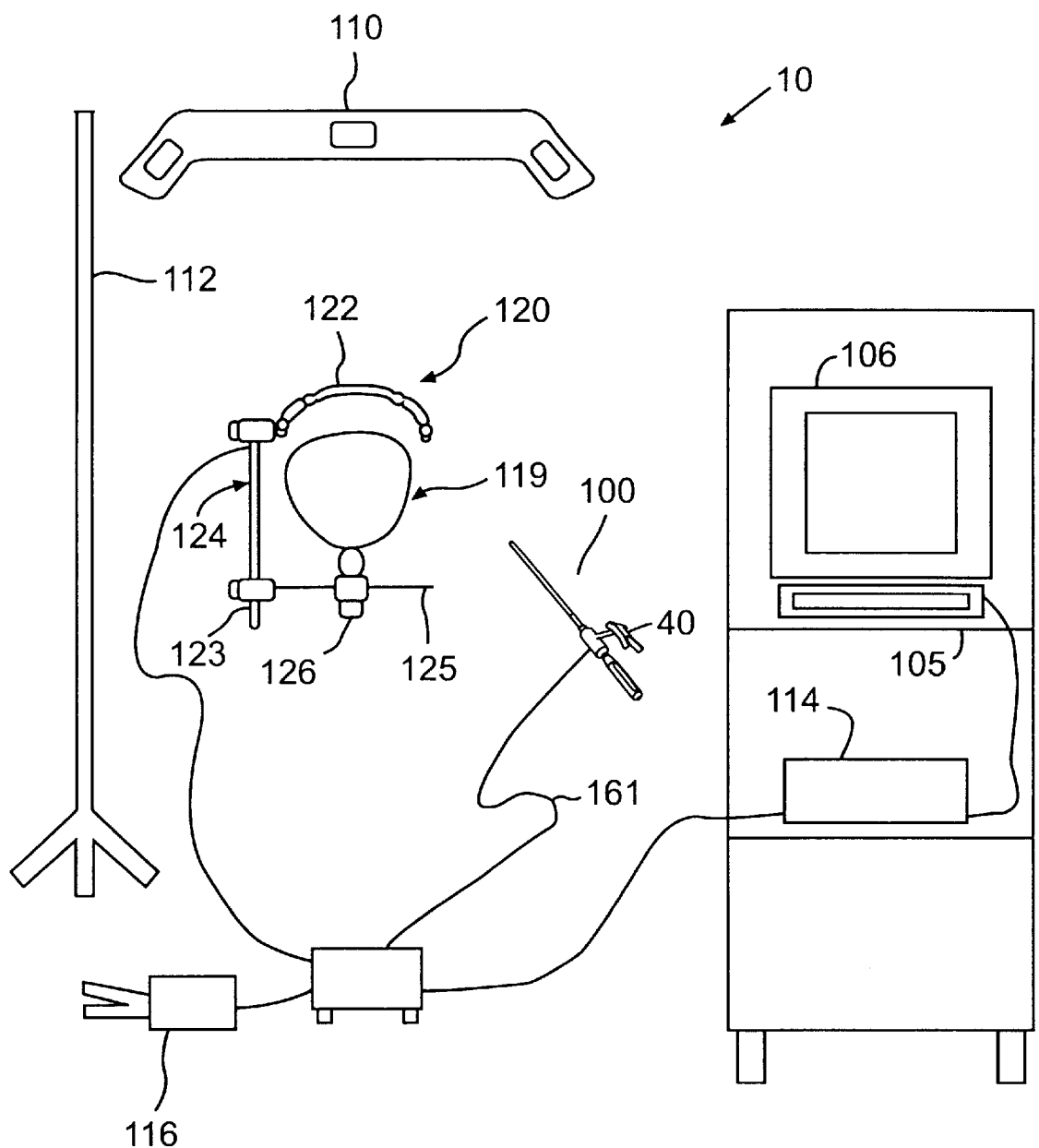
FIG. 1 is a schematic front view of a computer assisted image guided surgery system used with an instrument according to the present invention.

Reference will now be made in detail to the present preferred embodiments of the invention, examples of which are illustrated in the accompanying drawings. Wherever possible, the same reference numbers are used in the drawings and the description to refer to the same or like parts.

The medical instrument of the present invention is shown generally at 10 in FIG. 1. Instrument 100 can be used in many known computer assisted image guided surgical navigation systems such the system shown in FIG. 1 and disclosed in PCT application Ser. No. PCT/US95/12984 (Publication No. WO 96/11624) to Bucholz et al., incorporated herein by reference. A computer assisted image guided surgery system, shown at 10, generates an image for display on a monitor 106 representing the real time position of a body part and the position of instrument 100 relative to the body part.

An image may be generated on monitor 106 from an image data set stored in a controller, such as computer 108, usually generated preoperatively by some scanning technique such as by a CAT scanner or by magnetic resonance imaging. The image data set and the image generated have reference points for at least one body part. The reference points for the particularly body part have a fixed spatial relation to the particular body part.

System 10 also generally includes a processor for processing image data, shown as digitizer control unit 114. Digitizer control unit 114 is connected to monitor 106, under control of computer 108, and to instrument 100. Digitizer 114, in conjunction with a reference frame arc 120 and a sensor array 110 or other known position sensing unit, tracks the real time position of a body part, such as a cranium shown at 119 clamped in reference frame 120, and an instrument 100. Reference frame 120 has emitters 122 or other tracking means that generate signals representing the position of the various body reference points. Reference frame 120 is fixed spatially in relation to a body part by a clamp assembly indicated generally at 124,125, and 126. Instrument 100 also has a tracking device shown as an emitter array 40 which generates signals representing the position of the instrument during the procedure.

Sensor array 110, mounted on support 112, receives and triangulates the signals generated by emitters 122 and emitter array 40 in order to identify during the procedure the relative position of each of the reference points and the instrument. Digitizer 114 and computer 108 may then modify the image date set according to the identified relative position of each of the reference points during the procedure. Computer 108 may then generate an image data set representing the position of the body elements and the instrument during the procedure. System 10 may also include a foot switch 116 connected to instrument 100 and digitizer 114 for controlling operation of the system. The structure and operation of an image guided surgery system is well known in the art and need not be discussed further here.

Figure 2:
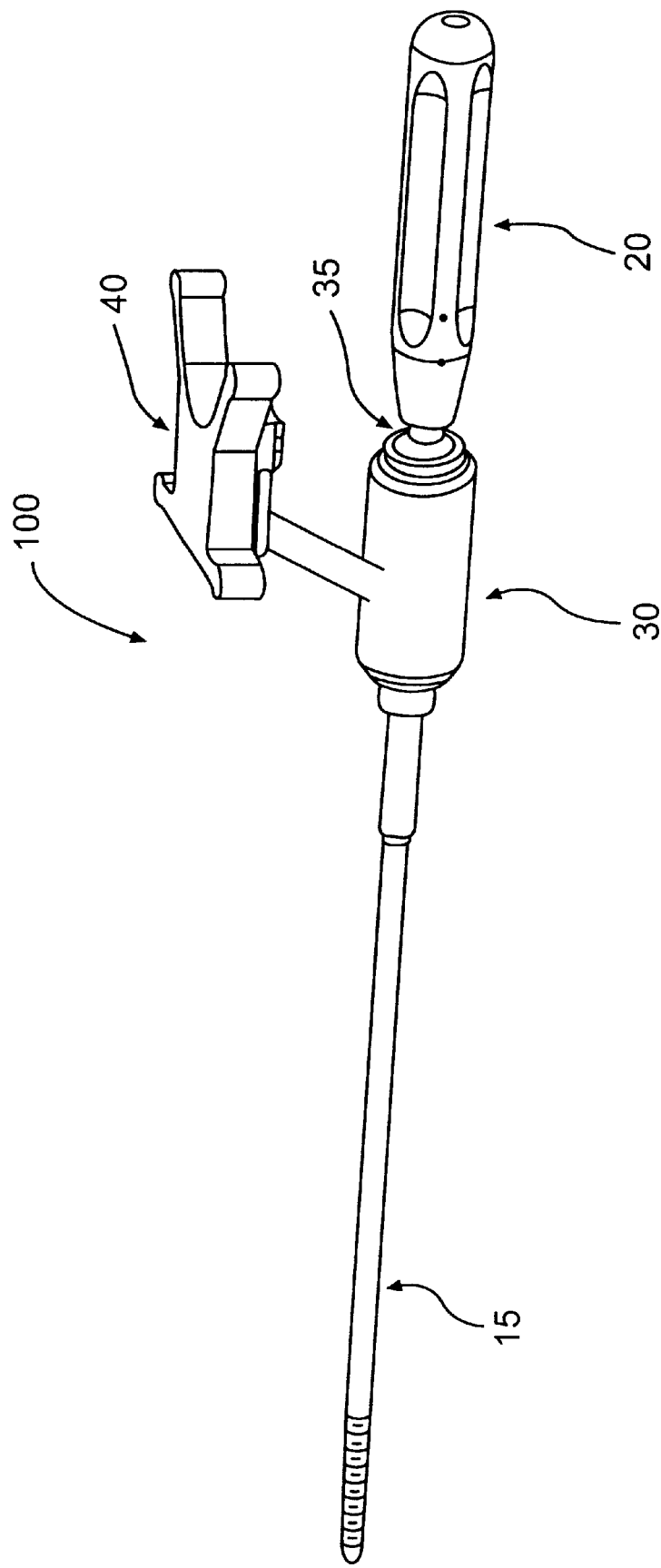
FIG. 2 is a perspective view of an instrument according to the present invention.
Figure 3:
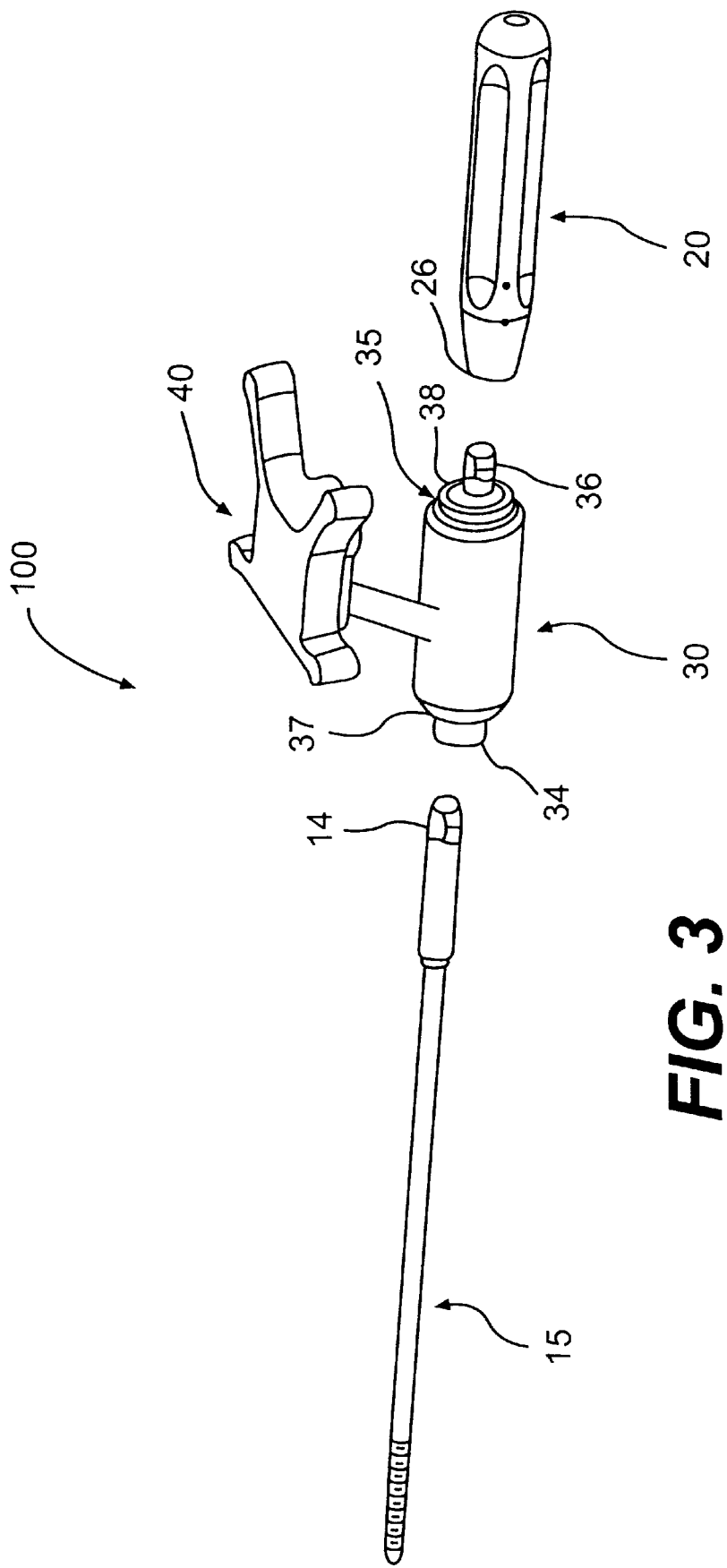
FIG. 3 is an exploded view of the instrument shown in FIG. 2.

Referring to FIGS. 2 and 3, an instrument according to the present invention is shown at 100. Instrument 100 includes a guide member 30, an interchangeable instrument tip 15, and an interchangeable driving handle 20.

Figure 5:
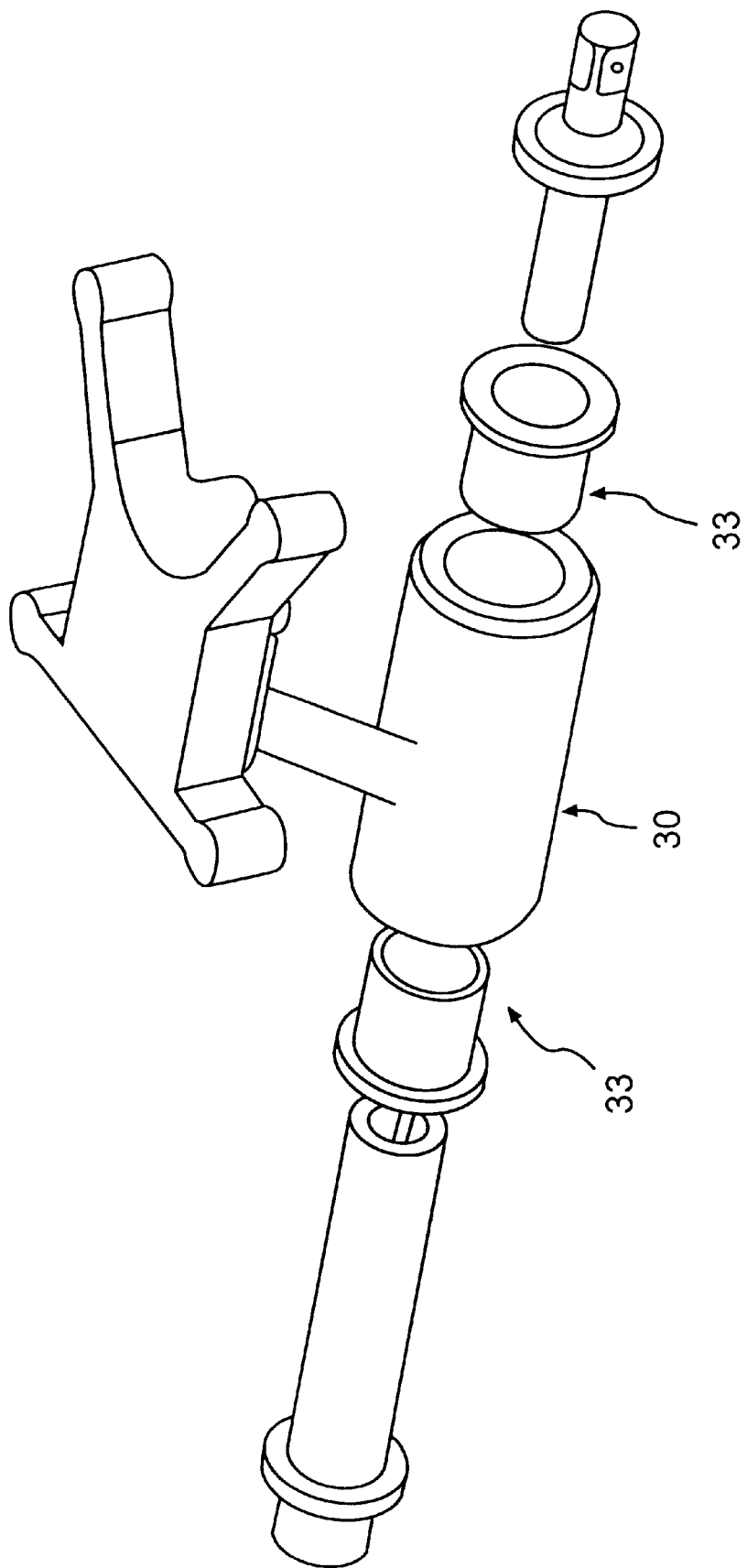
FIG. 5 is an exploded view of the portion of the instrument shown in FIG. 4.

A drive shaft 35 is housed within guide member 30 and is removably connected to an end, here the proximal end 37, to surgical instrument tip 15 and at the other end, here the distal end 38, to driving handle 20 such that torque applied manually or by motorized means to drive handle 20 is transmitted to drive shaft 35 which in turn is transmitted to tip 15. Drive shaft 35, while it could be extractable such as for service, is fixable axially in relation to guide member 30, but is rotatable within guide member 30. As shown in FIG. 5, bushings 33 may be provided at each end of guide member 30 to ensure smooth motion between drive shaft 35 and guide member 30. Guide member 30 is preferably made of stainless steel, but can also be made of titanium, aluminum or plastic. Shaft 35 is preferably made from stainless steel, titanium, or aluminum.

Figure 4:
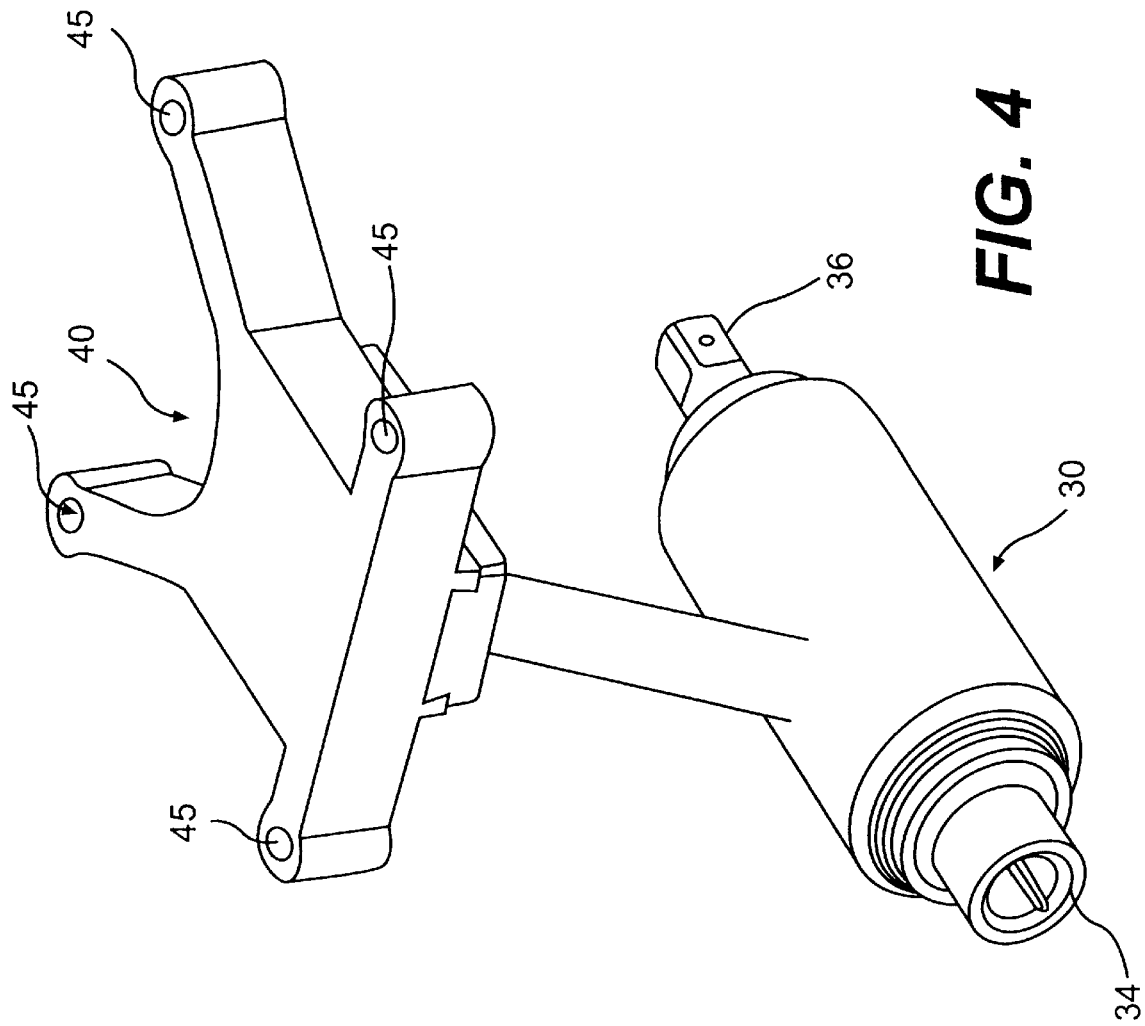
FIG. 4 is a view of a portion of the instrument shown in FIG. 2.

Instrument 100 further includes a tracking device such as emitter array 40 attached to guide member 30 for tracking the location and trajectory of instrument 100. As shown in FIG. 4, array 40 is equipped with a plurality of emitters or tracking means 45, preferably four emitters, for generating a signal representing the trajectory of instrument 100 and the depth of instrument tip 15. Preferably emitters 45 are light emitting diodes; however, other tracking devices known in the art capable of being tracked by a corresponding sensor array are within the scope of the invention. For purposes of illustration, not limitation, the tracking device may generate signals actively such as with acoustic, magnetic, electromagnetic, radiologic, and micropulsed radar systems, or passively such as with reflective surfaces.

Drive handle 20 and instrument tip 15 are shown as modular units that can be attached to drive shaft 35 with corresponding and interlocking male and female socket joints. As shown in FIGS. 3 and 4, drive shaft 35 has a female socket joint 34 for connection with a male socket 14 on tip 15, and drive shaft 35 has a male socket joint 36 for connection with a female socket joint 26 on drive handle 20. With the use of male and female socket joints, various instrument tips and various type and sized drive handles can be easily interchangeable. Instrument tip 15 could be any of a variety of instruments used in surgery such as taps, awls, and shaped tools for interacting with a work piece, such as a screwdriver for driving screws. Drive handle 20 could be any number of existing or specially designed handles and could be ratcheting, nonratcheting or motorized. Instrument tip 15 and drive handle 20 could also be permanently attached to drive shaft 35. Other suitable connection means are within the scope of the invention as well.

In operation, torque applied to drive handle 20 is transmitted through drive shaft 35 to instrument tip 15. Because drive shaft 35 is fixed axially in relation to guide member 30, guide member 30 can remain stationary while drive shaft 35 rotates without translating along the axis of drive shaft 35. The relationship between array 40 and the axis of drive shaft 35, therefore, remains constant. Instrument tip 15 is also fixed axially in relation guide member 30. As a result, the relationship between array 40 and instrument tip 15 also remains constant. Because the relationship between array 40 and tip 15 is constant, the signals emitted by emitters 45 can be used by the computer assisted image guided surgical navigation system to inform the surgeon of the position of instrument 100, indicating both the trajectory or orientation in three dimensional space of instrument 100 and the length of travel along the trajectory, i.e., the depth instrument tip 15 has been inserted into a body part.

It should be recognized that other variations or modifications may be made to provide an instrument that has an emitter array fixed axially relative to the instrument tip while allowing the instrument tip to rotate relative to the emitter array. For example, guide member 30 may also be integral with instrument tip 15 and/or drive handle 20. The array could then be fixed axially relative to the instrument and means could be provided to allow rotation of the instrument relative to the array.

As discussed above, a variety of different instrument tips may be easily interchanged on instrument 100. To use these different instrument tips, information concerning the dimensions of the different tips may be entered into computer 108. As a result, computer 108 can process the various image data for the specific instrument tip being used so that system 10 tracks the depth of the tip being used or, in the case of a screwdriver, so that system 10 tracks the depth of the screw being inserted.

System 10 may also be provided with a mechanism to prevent the system from operating after a new tip has been connected until computer 108 has been recalibrated. For example, an electromechanical switch, or other suitable sensors, could be provided on instrument 100 to provide a signal to computer 108 indicating that instrument tip 15 has been removed from instrument 100 or that a new instrument tip 15 has been coupled to instrument 100. The switch is preferably a micro switch but can be embodied by any suitable electrical or electromechanical device or sensing device capable of providing a signal in response to attachment or detachment at a particular point on guide member 30 or tip 15.

The switch may be automatically actuated when tip 15 is removed or coupled to instrument 100. Computer 108 may be operably connected to the switch, such as through cable 161, and is responsive to the operation of the switch. Alternatively, if a wireless instrument is used such as one with passive reflective surfaces in place of LED emitters, any suitable form of communication known in the art can be used. An alarm or other indication of some type, such as a message or display on monitor 106, may be generated by computer 108 indicating to the user that tip 15 has been changed. The computer 108 may further prevent the system from operating until the system has been recalibrated for the new instrument tip. Recalibration may be accomplished by touching the instrument tip to a known reference point. Recalibration of the instrument tip can be positively confirmed by means of a light emission from the emitter array 40 detected by sensor array 110 and triangulated to determine the position of the instrument tip. Alternatively, the dimensions of the instrument or tool type may be entered into computer 108 or selected from a pre-programmed list of tool dimensions or tool types. Further, recalibration could be accomplished by a fiber optic device for reading a bar code on the instrument tip, or by any other suitable recalibration technique.

It will also be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A trackable medical instrument for use in a computer assisted image guided surgery system having a digitizer for tracking the position of the instrument in three dimensional space and a display providing an indication of the position of the instrument with respect to images of a body part take preoperatively, the instrument comprising:
   a guide member having an emitter array mounted thereon for being tracked by a digitizer; and
   a drive shaft contained within the guide member, the drive shaft having a longitudinal axis and a proximal and a distal end, the drive shaft being rotatable within the guide member while being fixable within the guide member in a direction of the longitudinal axis, the proximal end of the drive shaft having a first connector for interchangeably receiving at least one drive source for transmitting torque to the drive shaft causing rotation of the drive shaft relative to the guide member, and the distal end having a second connector for interchangeably receiving at least one instrument tip.

2. The instrument according to claim 1, further comprising at least one instrument tip for removable connection to the distal end of the drive shaft.

3. The instrument according to claim 2, wherein the at least on drive source comprises a drive handle for removable connection to the proximal end of the drive shaft for transmitting torque to the drive shaft and the instrument tip to cause rotation of the instrument tip.

4. The instrument according to claim 3, wherein the drive handle and the drive shaft include a male-female socket joint to removably connect the drive shaft to the drive handle.

5. The instrument according to claim 3, wherein the drive handle includes a ratchet.

6. The instrument according to claim 3, wherein the drive handle includes a motor for imparting torque to the drive shaft.

7. The instrument according to claim 2, wherein the instrument tip and the drive shaft include a male-female socket joint to removably connect the drive shaft to the instrument tip.

8. The instrument according to claim 2, wherein the instrument tip is an awl.

9. The instrument according to claim 2, wherein the instrument tip is a tap.

10. The instrument according to claim 2, wherein the instrument tip has a shaped end for mating with a workpiece to be rotated by said drive shaft.

11. The instrument according to claim 2, wherein the instrument tip is a drill bit.

12. The instrument according to claim 1, wherein the emitter array includes at least one LED array for emitting light signals.

13. The instrument according to claim 12, wherein the LED array includes a base and a plurality of LED emitters disposed on the base.

14. The instrument according to claim 1, wherein at least one bushing is provided in the guide member to reduce friction between the guide member and drive shaft.

15. The instrument according to claim 1, wherein the instrument includes a sensor which senses the removal and connection of an instrument tip to the instrument.

16. The instrument according to 15, wherein the sensor includes an electromechanical switch on the guide member electrically connected to the system.

17. A trackable medical instrument for use in a computer assisted image guided surgery system having a digitizer for receiving signals representing a position of the instrument during surgery, a computer for processing the signals received, and a display for providing an image representing the position of the instrument in three dimensional space during surgery, the instrument comprising:
   guiding means for guiding the instrument in three dimensional space, the guiding means including signaling means for providing a signal representing the trajectory of the instrument and the location of the instrument; and
   driving means for driving the instrument contained within the guiding means, the driving means having a longitudinal axis and being fixable in relation to the guiding means in a direction of the longitudinal axis while being rotatable in relation to the guiding means, the driving means having a first end adapted to interchangeably receive at least one medical instrument tip and an opposite end adapted to interchangeably receive at least one drive source.

18. The instrument according to claim 17, wherein the instrument includes a sensing means for sensing the removal and the connection of an instrument tip to the instrument.

19. The instrument according to 18, wherein the sensing means includes an electromechanical switch on the guiding means connected to the means for processing.

20. The instrument according to claim 17, wherein the guiding means comprises a housing for receiving the driving means, the driving means being rotatable within the housing while being retained axially within the housing.

21. The instrument according to claim 20 wherein the signaling means comprises an LED array.

22. The instrument according to claim 21, further comprising an instrument tip for connection to the first end of the driving means.

23. The instrument according to claim 22, further comprising a drive handle for connection to the opposite end of the driving means for transmitting torque to the instrument tip to cause rotation of the instrument tip.

24. The instrument according to claim 20, wherein the driving means comprises a drive shaft having mating connectors on both ends for connection to corresponding connectors disposed on an instrument tip and a drive source.

25. The instrument according to claim 24, wherein at least one bushing is provided between the housing and the drive shaft to reduce friction between the guide handle and drive shaft.

26. The instrument according to claim 22, wherein the instrument tip is an awl.

27. The instrument according to claim 22, wherein the instrument tip is a tap.

28. The instrument according to claim 22, wherein the instrument tip has a shaped end for mating with a workpiece.

29. A trackable medical instrument for use in a computer assisted image guided surgery system having a digitizer for tracking the position of the instrument in three dimensional space and a display providing an indication of the position of the instrument with respect to images of a body part take preoperatively, the instrument comprising:

a guide member having an emitter array mounted thereon for being tracked by a digitizer;

a drive shaft contained within the guide member, the drive shaft having a longitudinal axis and a proximal and a distal end, the drive shaft being rotatable within the guide member while being fixable within the guide member in a direction of the longitudinal axis;

an instrument tip extending from the proximal end of the drive shaft; wherein the instrument tip rotates freely relative to the guide member while being fixable axially relative to the guide member; and a drive handle extending from the distal end of the drive shaft for guiding the instrument, including the guide member, and for imparting rotary motion to the drive shaft and the instrument tip independent of the guide member.

30. The instrument according to claim 29, further comprising a proximal coupler for interchangeably coupling the drive source to the drive shaft.

31. The instrument according to claim 30, wherein the proximal coupler comprises a male-female socket joint disposed on the drive shaft and the drive source to removably connect the drive source to the drive shaft.

32. The instrument according to claim 29, wherein the drive handle includes a ratchet.

33. The instrument according to claim 29, wherein the drive handle includes a motor for imparting rotary motion to the drive shaft.

34. The instrument according to claim 29, further comprising a distal coupler for interchangeably coupling the instrument tip to the drive shaft.

35. The instrument according to claim 34, wherein the distal coupler includes a male-female socket joint disposed on the drive shaft and the instrument tip to removably connect the instrument tip to the drive shaft.

36. The instrument according to claim 29, wherein the instrument tip is an awl.

37. The instrument according to claim 29, wherein the instrument tip is a tap.

38. The instrument according to claim 29, wherein the instrument tip has a shaped end for mating with a workpiece to be rotated by said drive shaft.

39. The instrument according to claim 29, wherein the instrument tip is a drill bit.

40. The instrument according to claim 29, wherein the emitter array includes at least one LED array for emitting light signals.

41. The instrument according to claim 29, wherein the at least one LED array includes a base and a plurality of LED emitters disposed on the base.

42. The instrument according to claim 29, wherein at least one bushing is provided in the guide member to reduce friction between the guide member and drive shaft.

43. A trackable medical instrument for use in a computer assisted image guided surgery system having a digitizer for tracking the position of the instrument in three dimensional space and a display providing an indication of the position of the instrument with respect to images of a body part taken preoperatively, the instrument comprising:

a guide member having a tracking device mounted thereon for being tracked by a digitizer;

a drive shaft contained within the guide member, the drive shaft having a longitudinal axis and a proximal and a distal end, the drive shaft being rotatable within the guide member while being fixable within the guide member in a direction of the longitudinal axis;

an instrument tip extending from the proximal end of the drive shaft; wherein the instrument tip rotates freely relative to the guide member while being fixable axially relative to the guide member; and a drive handle extending from the distal end of the drive shaft for guiding the instrument, including the guide member, and for imparting rotary motion to the drive shaft and the instrument tip independent of the guide member.

44. The instrument according to claim 43, wherein the tracking device includes a passive signal generator.

45. The instrument according to claim 44, wherein the instrument comprises at least one reflective surface for reflecting signals to be tracked by the digitizer.

46. The instrument according to claim 44, wherein the instrument comprises at least three reflective surfaces for reflecting signals to be tracked by the digitizer.

47. The instrument according to claim 43, further comprising a proximal coupler for interchangeably coupling the drive source to the drive shaft.

48. The instrument according to claim 47, wherein the proximal coupler comprises a male-female socket joint disposed on the drive shaft and the drive source to removably connect the drive source to the drive shaft.

49. The instrument according to claim 43, further comprising a distal coupler for interchangeably coupling the instrument tip to the drive shaft.

50. The instrument according to claim 49, wherein the distal coupler includes a male-female socket joint disposed on the drive shaft and the instrument tip to removably connect the instrument tip to the drive shaft.

\* \* \* \* \*